United States Patent [19]

Jawad et al.

[11] Patent Number: 5,239,175
[45] Date of Patent: Aug. 24, 1993

[54] COLOR MONITORING WITH DATA STORAGE MEANS

[75] Inventors: Sajad M. Jawad; John F. Alder, both of Cheshire, England

[73] Assignee: The Secretary of State for Defence in Her Britannic Majesty's Government of the United Kingdom of Great Britain and Northern Ireland, London, England

[21] Appl. No.: 828,814

[22] PCT Filed: Jun. 15, 1990

[86] PCT No.: PCT/GB90/00924
§ 371 Date: Jan. 29, 1992
§ 102(e) Date: Jan. 29, 1992

[87] PCT Pub. No.: WO90/15972
PCT Pub. Date: Dec. 27, 1990

[30] Foreign Application Priority Data

Jun. 15, 1989 [GB] United Kingdom ............... 8913800

[51] Int. Cl.$^5$ ............................................. G01J 3/50
[52] U.S. Cl. ................................. 250/226; 250/205; 250/227.23
[58] Field of Search ............ 250/205, 226, 208.2, 250/227.18, 227.23

[56] References Cited

U.S. PATENT DOCUMENTS

| | | | |
|---|---|---|---|
| 3,910,701 | 10/1975 | Henderson et al. | 356/39 |
| 4,281,245 | 7/1981 | Brogardh et al. | 250/205 |
| 4,529,875 | 7/1985 | Brogardh et al. | 250/227.23 |
| 4,681,454 | 7/1987 | Breemer | 250/205 |
| 4,760,250 | 7/1988 | Loeppert | 250/227 |
| 4,845,647 | 7/1989 | Dils et al. | 250/227.23 |
| 5,021,647 | 6/1991 | Tatsuno et al. | 250/205 |

FOREIGN PATENT DOCUMENTS

| | | |
|---|---|---|
| 0109686 | 5/1984 | European Pat. Off. |
| 0319769 | 1/1989 | European Pat. Off. |
| 0139769 | 6/1989 | European Pat. Off. |
| A8701491 | 6/1987 | Netherlands |
| WOA88/10462 | 12/1988 | PCT Int'l Appl. |
| 2165642A | 4/1986 | United Kingdom |

Primary Examiner—David C. Nelms
Attorney, Agent, or Firm—Nixon & Vanderhye

[57] ABSTRACT

Color changes in a target, such as a chemical sensor using a colorchanging indicator reagent to detect the presence of a poisonous gas, are continuously monitored by reflecting the target (10) on to a sensor (16) light originating from first one and then another light source (12a, 12b, etc), each having a different, known emission wavelength. In each cycle, direct light from the appropriate source is also collected by another sensor (14), connected in a closed loop (26) with circuitry in which the emission intensity is compared with a known reference value (38) and which adjusts the emission intensity so as to stabilize it at this constant reference value. Once this is stabilized, the reflected light intensity signal is passed to a data store (20), after which a divider (22) produces an output signal (36) representing the ratio of the reflected light intensities in two separate cycles originating from two different light sources (12a, 12b, etc). The conduct of each cycle is controlled by timing means (18). Where there are two light sources, the wavelength of the second (12b) is outside the response range of the target, that of the first (12a) being at or near the peak target response, so that all the divider output signals represent successive values of actual reflected light intensity. These signals can be processed to show the rate of color change in the target and used to operate e.g. an alarm.

12 Claims, 3 Drawing Sheets

COLOR MONITORING WITH DATA STORAGE MEANS

BACKGROUND OF THE INVENTION

1. Field of the Invention

This invention relates to apparatus and methods for monitoring colour changes in what will be referred to herein as a target, i.e. anything in or on which a change of colour may take place. The term "colour" is to be understood to mean the wavelength of light, emitted or reflected according to the context, whether or not it happens to be in the visible part of the spectrum.

2. Discussion of Prior Art

The problem of detecting over a substantial period of time the changes in chemical composition occurring in a gas or liquid flow, or indeed the detection of the change in any physical quantity which can be made to manifest itself as a colour change, is advantageously addressed by apparatus for monitoring colour changes. Such apparatus requires a high level of stability and fault tolerance if it is to be in operation over a long period of time.

One known system that can be applied to the measurement of absolute colour intensities over a period of time is an optical device for measuring physical quantities and is disclosed in UK Patent Application No. 2,025,608 (corresponding to U.S. Pat. No. 4,281,245). This device comprises generally two sources of different wavelengths of light which are optically connected to an optical transducer. The transducer comprises an optical filter having spectrally varying absorbing, transmitting or reflecting properties which are influenced by the physical property in question. The transducer is assembled in such a way as to ensure that one of the wavelengths of light (the reference signal) is substantially less dependant on the measured quantity than the other (the measuring signal). The corresponding two output signals of the transducer are then divided and in this way a stablised measurement is obtained.

This known device is capable of measuring a sequential series of absolute values of the physical quantity over a period of time. Errors common to the paths of both wavelengths of light are removed by the divider, however other errors which vary with time will be incorporated into the measurements obtained obscuring genuine changes in the value of the physical quantity. Such errors can be caused by drifts in the sensitivity of the sensors and in the intensity of the light source due to ageing and other inconsistencies which are likely to occur over a substantial period of time. One way of overcoming this is by repeated calibration procedures which would necessarily halt the continuous monitoring of the target and is therefore inconvenient.

SUMMARY OF THE INVENTION

The present invention overcomes this problem by the provision of signal processing means for comparing successive output signals from the divider means to give a resulting signal representing the degree of change or rate of change of successive measurements. This eliminates errors which change with time but whose rate of change with time is relatively constant, as is the nature of the errors that are likely to occur over a substantial period of time, as mentioned above. Furthermore this apparatus provides a versatile system for continuously monitoring colour changes in a target, reliably, accurately and with simple signal processing.

According to the invention in a first aspect, such an apparatus comprises:

a plurality of light sources, each arranged for intermittent operation and each having effectively a single emission wavelength different from that of the other source or sources, timing means for causing each source to operate in turn, and a reflected light sensor, for receiving light transmitted by the sources but reflected from the target, characterised in that the apparatus additionally comprises:

a direct light sensor substantially identical to the reflected light sensor, for receiving light directly from the sources, the direct light sensor being connected in a closed energy loop with the light sources and with reference means for stabilising the source intensity of the emission from each source at a predetermined level, a plurality of data stores, each arranged to receive from the reflected light sensor a signal representing the intensity of the reflected light at a respective one of the emission wavelengths, divider means for receiving the information held in the data stores and for giving sequential output signals each representing the ratio of two said reflected light intensities, and signal processing means having means for receiving and storing a predetermined number of successive output signals from the divider means and means for comparing these signals to give an output signal representing the degree and/or rate of change in the ratios of the reflected light intensities, whereby a change in the ratios of the reflected light intensities will correspond to a change in the colour of the target such that the colour monitoring apparatus continuously monitors colour changes in the target.

The present invention enables colour changes to be continuously monitored by producing a sequence of signals which being ratiometric, eliminates errors between the reflected light signals. Furthermore, the subsequent subtraction of successive ratiometric signals removes all errors which change with time but whose rate of change with time is relatively constant. Therefore the present invention is highly suited to the monitoring of colour changes over a substantial period of time, as it is able to eliminate the errors that are likely to result from the ageing of constituent components.

The purpose of the closed loop, with the direct light sensor which receives only incident light (from each light source in turn) is to stabilise the source intensity each time a light source is energised, before the appropriate data store or stores release a signal to the divider means. In this way each successive reflected light signal derives from an emission having the same source intensity as its predecessors.

Accordingly, the apparatus preferably includes enabling means responsive to a signal from the reference means for permitting a signal to be received from the reflected light sensor by said data store only when the source intensity of the corresponding light source has been stablised.

Methods for the continuous stabilisation of light source intensity are known in the prior art which result in a light source intensity that fluctuates about the desired level, which in this application is a disadvantage.

It is for this reason that the present invention preferably includes a closed energy loop which causes the light source intensity to be gradually increased to the desired level, at which it is held, and only then allows the signal from the reflected light sensor to be released to the relevant data store. This ensures that the light source is highly stable and of the desired intensity when a measurement is taken so that the reflected signal received by the data store is highly stablised.

Among possible applications of the apparatus according to the invention are those which give a quantitative measure of colour changes, for example changes over a period of time and/or over a scanned area, i.e. the difference between the colour value or intensity at one point on the scanned area and that at another point. Colour changes occurring with time may take place at a signal location: an example of this is in a chemical sensor of a kind in which an indicator reagent is used to betray the presence of a substance which causes this indicator to change colour, its colour intensity bearing a known relationship to the concentration of the substance being monitored. In an application of this kind it will in most cases be necessary to measure colour change at only one wavelength, so that only a single light source need be provided.

However, in order to provide a denominator (or numerator) for the quotient function produced by the divider means, a second light source is required so that two reflected light signals can be compared in each divider operation.

Thus, according to a preferred feature of the invention, the apparatus has two each of the said light sources and data stores, with one source having a first emission wavelength so that the intensity of light of the first emission wavelength reflected by the target changes by an amount directly related to the change of color of the target; and the other source having a second emission wavelength so that the intensity of light of the second emission wavelength reflected by the target is substantially unaffected by the change in color of the target, the divider being arranged to receive information from both data stores at once and to perform a signal division calculation thereon in each cycle of operation.

In this preferred feature of the invention, the light sources preferably comprise clusters of light emitting diodes (LED) of the same wavelength connected in parallel. Therefore should any of the light sources in the cluster fail, its share of the total light output would automatically be compensated for by the others in the cluster. This occurs because the closed energy loop ensures that the source intensity is at the desired value, by applying a greater voltage across the parallel connected LEDs. This happens automatically without interrupting or affecting the measurement cycle, thus providing an important fault tolerant feature to such a long term detection device.

Within the scope of the invention is an apparatus which includes the target itself, together with fibre optic connections that comprise a first connection, which is part of the closed energy loop, between the light sources and the direct light sensor, a second connection between the light sources and the target, and a third connection between the target and the reflected light sensor.

It will be appreciated that the apparatus is responsive to, and capable of measuring quantitatively, the intensity of light reflected from the target at a known wavelength at any given instant or at any given point on the target. However, there is no need whatsoever to measure the intensity of light incident on the target. The apparatus automatically compensates for any variations in incident light by using at least two light sources at difference wavelengths with two sensors, one of which (the direct light sensor) is used to enable the emission intensities of the light sources to be adjusted prior to each operation of the apparatus, always to exactly the same level. This leads to substantially simplification of the signal processing procedure.

It will also be noted that, even though continuous monitoring is afforded by the invention, the light sources are only energised intermittently. This greatly improves their life expectancy, and leads to greater reliability and reduced maintenance.

Many applications may require the apparatus to give an absolute measurement of colour intensity in the target, or at one point or each of a plurality of points on the target. In addition, or alternatively, it may be required to measure the rate of change of colour intensity, either between one point and another on the target or over a period of time. The invention enables all of these options to be grasped as desired, besides the benefits already mentioned or implied, such as elimination of all errors not related to the parameter actually being measured, simplified processing, and so on.

According to the invention in a second aspect, a method of continuously monitoring colour changes in a target comprises in sequence the steps of:

(i) directly a first emission of light having a first emission wavelength from a first source on to a first light sensor to give first output signals responsive to the intensity of the emitted light, and on to the target, and reflecting the first emission from the target to a second light sensor so as to give second output signals responsive to the intensity of the reflected light;

(ii) comparing the first output signals with a known reference value, increasing the first source intensity, i.e. the intensity of the light emitted from the first source, until it exactly equals the reference value, and preventing any further increase therein so as to stabilise the first source intensity;

(iii) when the said first source intensity is stablised, storing the second output signal then being given;

(iv) repeating steps (i) and (ii) but with a second emission of light from a second source having a second emission wavelength and a second source intensity, so that the first and second sensors give third and fourth output signals in place of the first and second output signals respectively;

(v) when the second source intensity is stabilised, storing the fourth output signal then being given;

(vi) dividing one of the stored second and forth signals by the other to produce a fifth output signal representing the ratio of intensities of reflected light derived from the first and second emissions;

(vii) timing the cycle comprising steps (i) to (vi) to take place over a predetermined period of time, and (viii) repeating the cycle comprising steps (i) to (vi) at least once and processing together the resulting succession of fifth output signals to give final output signals representing changes in the intensity of the light reflected from the target at at least one known wavelength, The first and second emission wavelengths being chosen to be difference from each other and each being effectively a single wavelength.

BRIEF DESCRIPTION OF THE DRAWINGS

This invention is broadly explained, and a preferred embodiment described by way of example, in the following description with reference to the accompanying drawings, in which.

DETAILED DESCRIPTION OF PREFERRED EMBODIMENT

Figure 1:
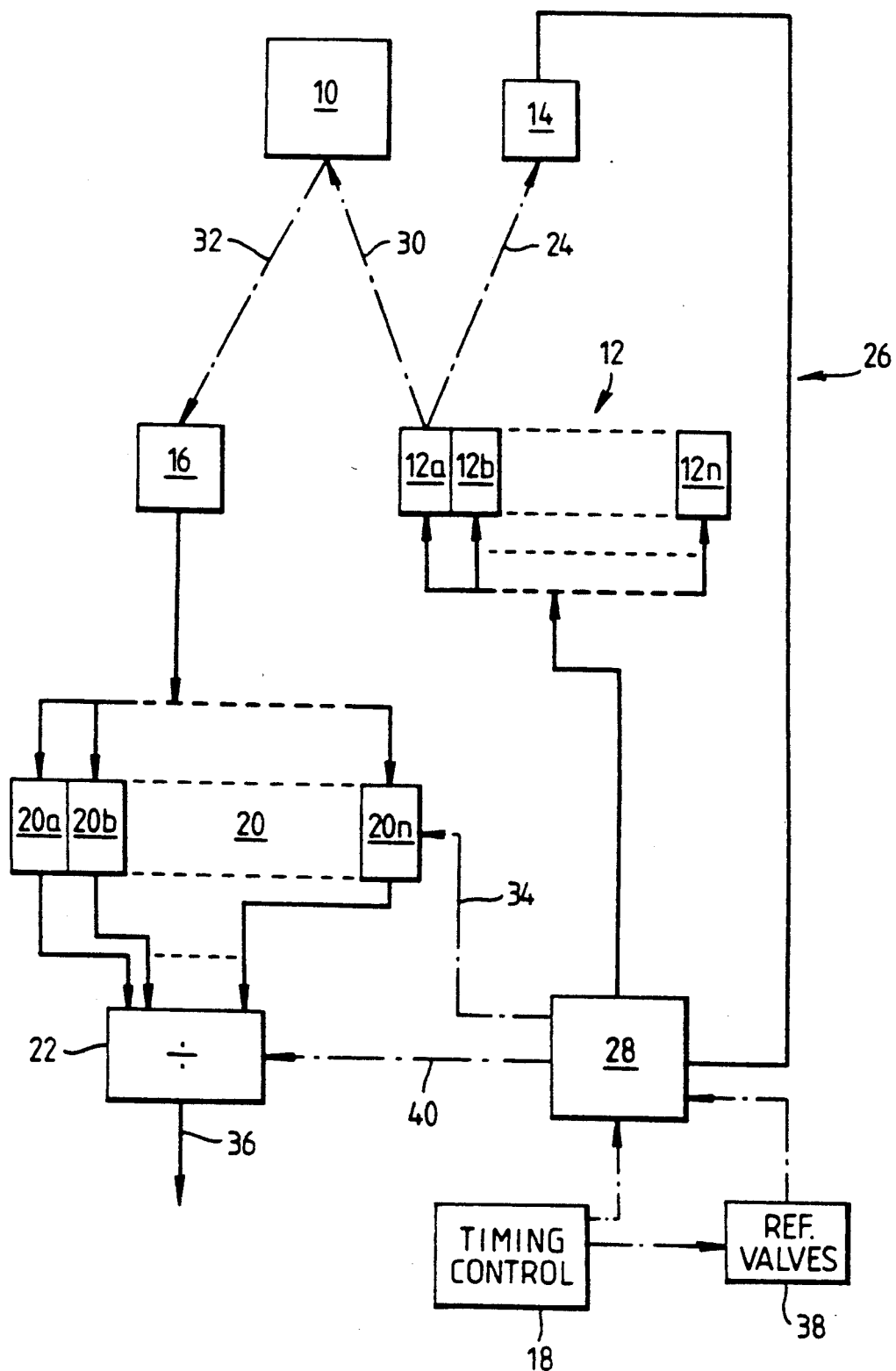
FIG. 1 is a diagram illustrating main features of a monitoring apparatus according to the invention.

Referring to FIG. 1, a target, a susceptible colour change which is to be monitored, is indicated at 10. The monitoring apparatus or colour monitor comprises a plurality of light sources 12, a first (direct) light sensor 14, a second (reflected) light sensor 16, timing control means 18, a set of data stores 20, and a divider 22.

The sensor 14 is arranged so as to receive incident light directly from the light sources 12 along a light path indicated at 24. This path 24 forms part of a closed energy loop generally indicated at 26. The energy in this loop is electrical energy except in the path 24. The loop 26 includes the sensor 14, appropriate circuitry 28, and the light sources 12 which are connected in parallel with each other. The other sensor 16 is arranged to receive light which is incident along a path 30 from the sources 12 on to the target 10, and which reflects it back to the sensor 16 along a light path 32. In response to the intensity of the reflected light received by the sensor 16, the latter transmits electrical signals to the data stores 20. There is one data stores 20 corresponding to each light source 12, and the data stores 20 are in parallel with each other. The divider 22 is arranged to calculate the ratio of the magnitudes of the signals from any two of the data stores 20. The divider is capable of giving a sequence of quotient signals at its output 36, each quotient signal representing the ratio of the output signals from two data stores 20 and therefore representing the relative intensities of two successive reflected light signals received by the sensor 16 from the target 10.

Each light source 12 is of a kind having effectively a single emission wavelength, which means in practice that it may transmit light within a very narrow band of emission wavelength. This band is different for each light source from those of the others. Each light source is also arranged for intermittent operation, and the timing means 18, through the circuitry 28, operates each source 12 in turn. A control function, indicated diagrammatically at 34, selects one of the data stores 20 according to which one of the light sources 12 is energised, in such a way that when a reflected light signal from that source reaches the sensor 16, it is the selected store 20 that receives the resulting output signal from the sensor 16. In this way, each of the data stores 20 is arranged to receive from the sensor 16 a signal representing the intensity of the reflected light at a respective one of the emission wavelengths.

In operation, suppose that the light source 12a is the first of the sources to energised. Its output intensity is gradually increased, being monitored continuously by the incident light sensor 14 until the output intensity reaches a predetermined reference value. Information representing this reference value for the characteristic emission wavelength a,b, ... n of each light source 12a,12b, ... 12n is passed as an output signal from a reference means 38 under the control of the timing means 18, to be compared in the circuitry 28 with the actual intensity signal received by the latter from the sensor 14. When the intensity of the incident light on the sensor 14 has reached the appropriate reference value, the source 12a is held at this value, and the data store 20a is enabled by the control 34 to record the output signal from the sensor 16 representing the intensity of the reflected light.

The source 12a is then switched off and the next source 12b switched on, the process then being repeated with the signal from sensor 16 being received by the next data store 20b; and so on until a cycle of operation is completed by a signal being received in the last data store 20n of light originating from the last source 12n. A new cycle of operation can then be started in the same way.

The closed loop 26 thus ensures that at any given steady emission wavelength a,b, ... n, the intensity of the light incident on the target 10 is always the same, so that the difference in intensity between one reflected light signal received by the sensor 16 and the next one at the same wavelength represents directly a change in the spectral absorbance of the target at that wavelength.

Once any two of the data stores 20 have received signals, corresponding to difference emission wavelengths, from the sensor 16, the divider 22 can be enabled, by a control function indicated diagrammatically at 40 and controlled from the circuitry 28, to compare the two values and produce a quotient signal at its output 36. Because this output signal represents a ratio, parameters common to the reflected light intensities at the two wavelengths concerned, particularly errors which may be due to environmental disturbance or other causes, can be shown to cancel out.

In addition, considering the case where the wavelength a of the light source 12a is one to which the target 10 does in fact respond by reflecting more or less light to the sensor 16 as it changes color, but where the wavelength b of the light source 12b is one to which the target does not respond and so reflects a substantially constant intensity of light to the sensor 16 as it changes color, then; the difference between the magnitudes of the ratiometric output signals from the divider 22, each derived from the light emitted by sources 12a and 12b, can be used to measure the change in the intensity of the reflected light originating at the source 12a alone. This facility is used to advantage in the apparatus shown in FIGS. 2 and 3.

Figure 2:
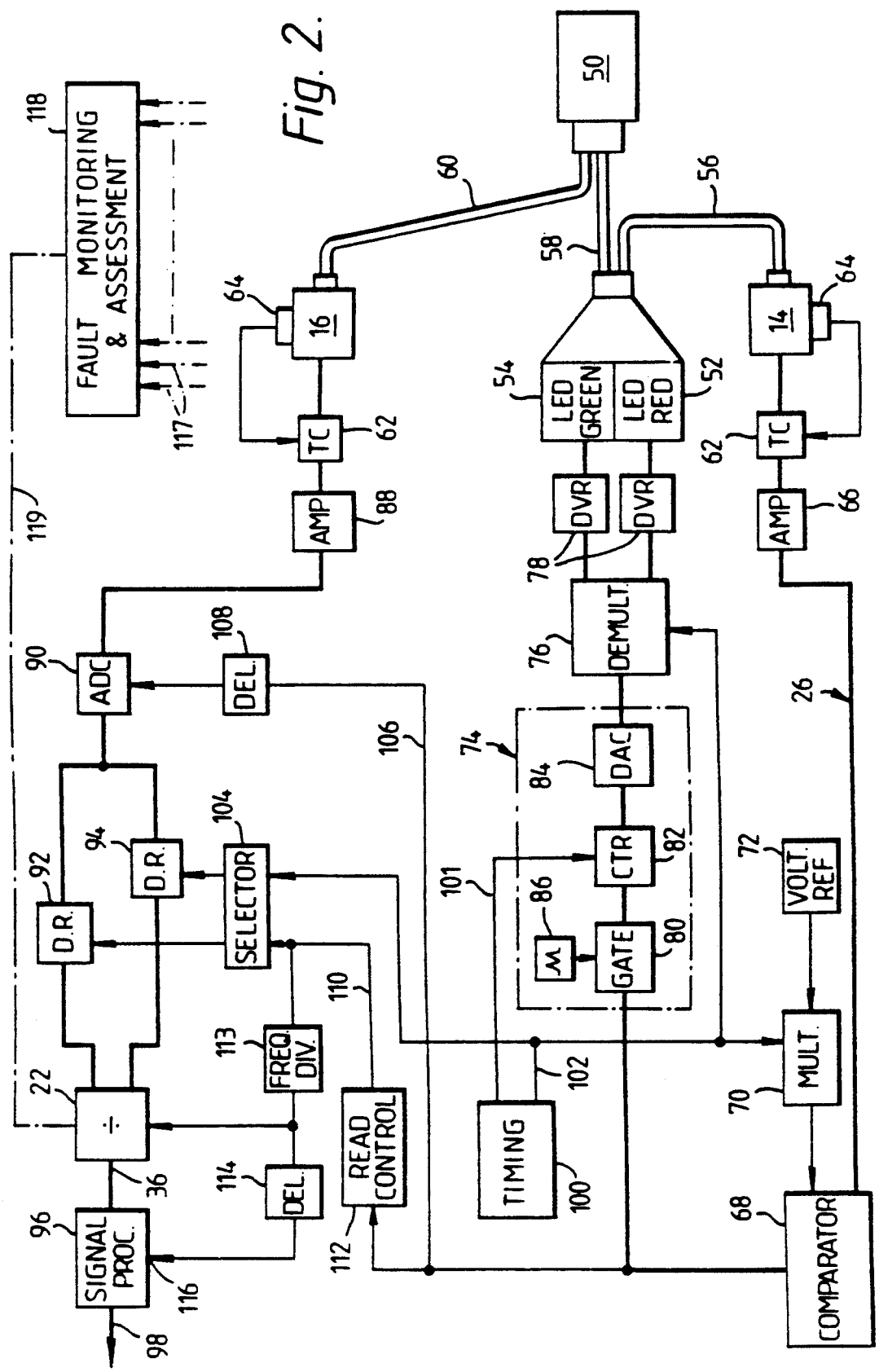
FIG. 2 is a simplified block diagram of a monitoring unit according to the invention, for detecting the approach of a poisonous gas.
Figure 4:
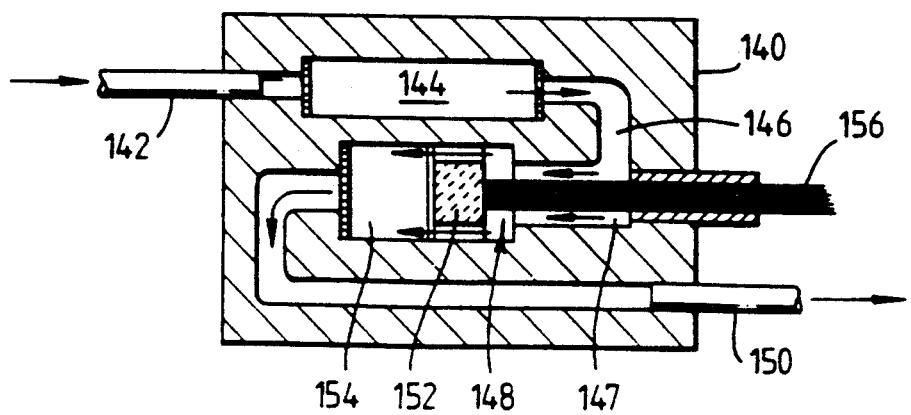
FIG. 4 is a schematic diagram of a chemical gas sensing device for use with the unit shown in FIG. 2.

Referring to FIG. 2, the target 50 is a chemical sensor for detecting the presence of hydrogen cyanide gas, and containing an indicator which, originally a pale buff colour, turns red in the presence of cyanogen chloride, with the colour intensity increasing as the concentration of the gas increases. The cyanogen chloride is made in a reactor comprising chloramine T coated on resin beads before the indicator reagent (FIG. 4). The monitor has a red light source 52 and a green light source 54, each of which consists of a cluster of light emitting diodes (LED) connected in parallel with each other and all emitting light at the same wavelength. As the indicator turns red on contact with the gas, it absorbs some of the green light received from the LED 54 while reflecting red light from the LED 52, in an intensity which increases as the intensity of the red coloration increases in the chemical sensor. The LEDs 52 and 54 are optically coupled to the incident light sensor 14 and the chemical sensor 50 through bundles, 56 and 58 respectively, of optical fibres, both bundles being common to both the LEDs 52 and 54. The sensor 50 is optically coupled to the reflected light sensor 16 through a bundle of optical fibres 60. The ends of the fibre bundles 58 and 60 at the sensor 50 are fully randomised so as to maximise even distribution of the incident light and to facilitate collection of the reflected light.

Each of the sensors 14 and 16 consists of a photodiode, having its output connected to a temperature compensating circuit 62 controlled by a temperature sensor 64 which is arranged adjacent to the light sensor 14 or 16 itself.

In the enclosed energy loop 26, output signals from the sensor 14 are delivered via the circuit 62 and an amplifier 66 to one of the two inputs of a comparator 68. The other input of the comparator 68 is connected via a multiplexer 70 with a voltage reference source 72, which feeds the multiplexer 70 with a voltage corresponding to the reference value of the intensity of red light and green light respectively required for the operation of the LEDs 52 and 54, in the same way as described above with reference to FIG. 1. The output from the comparator 68 is led to a ramp generator 74, and thence via a demultiplexer 76 to the respective driving units 78 of the LEDs 52 and 54. The loop 26 is completed by the optical coupling 56 between the LEDs and the sensor 14.

The ramp generator 74 includes, connected in the loop 26 itself, a gate 80, a binary counter 82, and a digital-to-analogue converter (DAC) 84. An independent sub-clock generator 86 is connected to the control input of the gate 80, the output of which is connected to the counter 82. The output of the latter is fed to the DAC 84, and that of the DAC to the input side of the demultiplexer 76.

The output side of the reflected light sensor 16 is connected, via its compensator 62 and an amplifier 88, to an analogue-to-digital converter (ADC) 90, and thence to the data stores corresponding to the data stores 20 in FIG. 1. In the embodiment shown in FIG. 2, these stores consist of two data registers 92 and 94 connected in parallel with each other. The register 92 stores signals from the sensor 16 corresponding to activation of the red LED 52, while the register 94 performs the same function when the green LED 54 is activated. The output sides of both data registers are connected to the input side of the divider 22, the output 36 of which leads to a signal processor generally indicated at 96, which uses the information fed to it by the divider 22 to produce output signals at 98. These are the final output signals of the monitor itself, and are used in any desired way, e.g. to operate an alarm to indicate the presence and/or increase in concentration of the poisonous gas, or to operate a visual indicator of some kind, or to control appropriate equipment, for example to close ventilators to prevent ingress of the gas. One embodiment of the processor 96 will be described later with reference to FIG. 3.

In FIG. 2, the timing means corresponding to the timing means 18 of FIG. 1 is generally indicated at 100. It has an output 101 connected to a control input of the binary counter 82. This timing control unit 100 also has a multiplexing control output 102, connected to control inputs of the multiplexer 70 and demultiplexer 76. It also leads to one of two inputs of a data selector 104 which has two outputs, connected to the control inputs of the "red" and "green" data registers 92 and 94.

Output signals from the comparator 68 are tapped from the loop 26 to perform two further control functions. One of these is the enabling function for the ADC 90, for which purpose a control input of the latter is connected to the loop 26 through a line 106 containing a delay circuit 108. A line 110 is connected between the loop 26 and the second input of the data selector 104, via a "read" control line 110 which includes a read control circuit 112. The output of the circuit 112 is connected directly to the data selector 104, and also leads to the input of a frequency divider 113, the output of which is connected to a control input of the divider 22 and, via a delay circuit 114, to a control input 116 of the signal processor 96.

The apparatus may also include appropriate fault monitoring and assessment circuitry, indicated diagrammatically at 118, which is arranged in known manner for monitoring the various functions of the apparatus and feeding appropriate disabling signals to the divider 22 via a line 119. Inputs to the circuitry 118 from individual parts of the monitor are indicated at 117.

Figure 3:
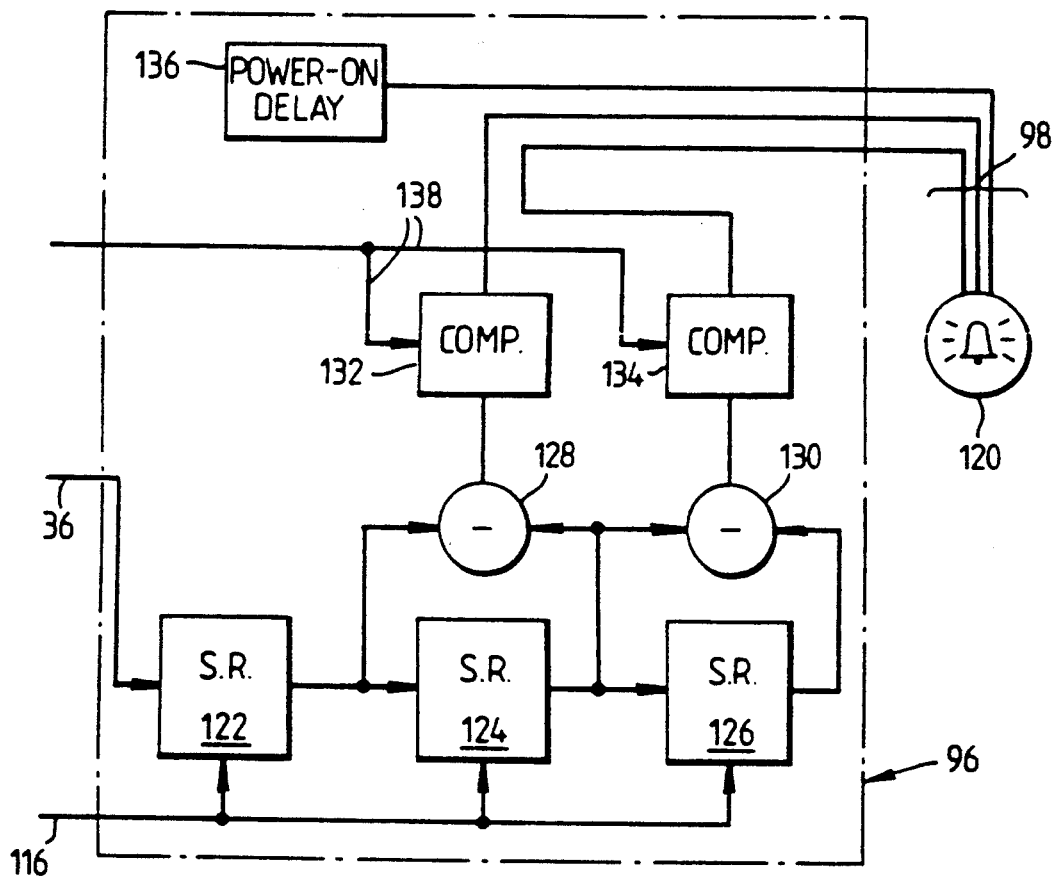
FIG. 3 is a simplified block diagram showing one example of an analyser for use in an apparatus such as that shown in FIG. 2.

FIG. 3 shows one form that the signal processor 96 may take. It is designed to process successive signals from the divider 22, received along the input line 36, and to activate an alarm 120 when those signals indicate the presence of a predetermined concentration of cyanide gas at the chemical sensor 50.

This processor 96 comprises three shift register units 122, 124 and 126 connected in series, each having a control input constituting the input 116. (FIG. 2). The main input line 36 leads into the unit 122. A first subtractor 128 is connected across the unit 124, and a second subtractor 130 across the unit 126. The outputs from the subcontractors are connected, via respective digital comparators 132 and 134, to the activating inputs for the alarm 120. A delay circuit 136 delays any operation of the alarm when the apparatus is first switched on, so as to inhibit the alarm from being activated by any transient signals at that time.

The apparatus of FIG. 2 operates as follows. It should be noted first of all that one of the functions of the multiplexing output at 102 from the timing control unit 100 is to select, via the multiplexer 70, which of the LED clusters 52, 54 is to be energised at any given instant. The control unit 100 may take any suitable form, but for the purposes of this description it will be assumed that it includes a master timing generator providing a square wave which is suitably modified into regular pulses of very short duration at the output 101, for control of the binary counter 82, and pulses at half the frequency of the master timing generator at the multiplexing output 102, these representing the time multiplexing control signal. It will also be assumed that the low or "space" part of this signal operates the reg LED 52, while the high or "mark" portion operates the green LED 54, and that when power is first switched on to the apparatus, it is the red LED 52 that operates first. For this latter purpose, the control unit 100 may include a delay line to ensure that, when power is switched on, the multiplexing control signal is in the appropriate state.

The gate 80 is enabled by the clock generator 86, so that the binary counter 82 starts to count up, its output being fed to the DAC 84 which produces an analogue voltage in the form of a linear rising staircase. This voltage is fed as an input signal via the demultiplexer 76 to the driver unit 78 of the red LED cluster 52, which starts to emit light received directly by the incident light sensor 14.

The multiplexing control signal at 102 sets the multiplexer 70 to select from the voltage reference means 72 the preset reference value for the intensity of red light, and a corresponding signal is fed by the multiplexer to the comparator 68. The rising voltage signal from the DAC results in a gradual increase in the intensity of the red light, and when this reaches the same value as the reference signal received from the multiplexer by the comparator 68, the output signal from the latter changes state in such a way as to disable the gate 80 and thereby prevent any further counting by the binary counter 82. As a result, the light produced by the LED 52 is stabilised at a value of intensity equal to the reference value.

After a short time delay controlled by the delay unit 108, the output signal from comparator 68, fed along the line 106, enables the ADC 90 to start conversion operation in the voltage signal received from the reflected light sensor 16 in response to the intensity (which may be zero) of the reflected red light received through the fibre optic coupling 60.

The control circuit 112 is arranged to produce a short control pulse after a preset time delay which begins as soon as the signal from the comparator 68, received by the circuit 112, indicates that the LED 52 is stabilised. At the end of this predetermined delay, the short control pulse from the circuit 112 is used, via the data selector 104, to instruct the "red" data register 92 to store the output signal received from the ADC 90.

The events occurring when the comparator inputs become equal in level are typically as follows. The output from the comparator 68 changes instantly from HIGH to LOW, which immediately disables the gate 80 and so inhibits the binary counter 82 from any further counting. The control circuit 112 may consist of a pair of monostable flip-flop circuits in series, such that when the comparator output signal changes state to LOW, the first of these circuits is triggered to go HIGH for a period of time slightly longer than the conversion time of the ADC 90. At the end of this period, the first monostable circuit goes LOW, which triggers the second monostable circuit to produce the short control pulse mentioned above.

After a predetermined period (which in this example will be assumed to be 7.5 seconds) from the initial of power to the apparatus, the master timing generator in the control unit 100 initiates a new timing period, which causes the multiplexing control signal at 102 to change state and the unit 100 to transmit a single short control pulse to the binary counter 82, which resets the latter to zero. This process selects the green LED cluster 54. The LED 54 is stabilised, and a signal stored in the "green" data register 94, in the same way as described above. The data registers 92 and 94 now hold signals corresponding to the intensity of the reflected red light and green light respectively. One cycle of operation is now complete, having taken 15 seconds. At this point, a further control pulse from the control unit 112 causes the frequency divider 113 to transmit a control signal to the divider 22, to enable the latter to produce its quotient output signal at 36 representing the ratio of the signals stored in the data registers 92 and 94.

Where the signal processor 96 shown in FIG. 3 is used, the delay circuit 114 (FIG. 2) caused a short delay, after which the same control signal from the frequency divider 113 is fed to the shift register unit 122, which causes the latter to store the signal received from the divider 22. A further signal will be received by the unit 122 every 15 seconds. Each time a new signal is received by the unit 122, the previous signal is transferred to the second shift register unit 124, while the previous signal in the unit 124 is similarly shifted into the shift register unit 126. The shift register unit outputs are subtracted from each other by the subtractors 128 and 130, and the difference is compared by the comparators 132 and 134 with a predetermined reference value supplied at a control input 138. If the difference signals received by the comparators from the subtractors 128 and 130 are both above this reference value, then the alarm 120 is activated.

Use of a signal processor such as the processor 96 of FIG. 3 enhances protection against spurious results by enabling any desired degree of "persistency" to be built into the apparatus, by virtue of the subtractors 128 and 130. With two subtractors as shown, persistency of results over two successive cycles of operation is obtained. The number of subtractors and shift registers can be increased so as to give any larger degree of persistency that may be required, in order to make absolutely certain that no spurious or freak results are taken into account.

The temperature sensors 64 are typically arranged to measure the temperature of the casing of the associated light sensor. The two light sensors may if desired be mounted side by side, with a common temperature sensor controlling both of the temperature control circuits 62.

The chemical sensor 50 may be of any suitable kind and will not be described in much detail here. It may be of a kind capable of detecting the presence of any specific gaseous substance in the atmosphere, or of specific pollutants either in the atmosphere or in any other gaseous or liquid environment (for example in a water supply system), provided the substance to be detected will undergo a chemical reaction with a suitable reagent such as to produce a colour change in the latter.

FIG. 4 shows purely diagrammatically, certain elements of a chemical sensor suitable for detecting the presence of hydrogen cyanide in the atmosphere. The chemical sensor 50 in FIG. 2 may be of this type. That shown in FIG. 4 has a hollow body 140 with an air inlet 142, leading in succession through a primary reaction chamber 144, a cross-passage 146, and an optic chamber 148 to an effluent output 150. Atmospheric air is drawn continuously through the chemical sensor, for example by an external pump (not shown) connected to the output 150.

The primary reaction chamber 144 contains a suitable oxidising reagent which reacts with any hydrogen cyanide in the air to produce cyanogen chloride. The resulting effluent gas passes via the cross-passage 146 into an upstream portion 147 of the optic chamber 148. The chamber 148 contains, downstream of the portion 147, an optical cell comprising a light receptor 152 and a secondary reaction chamber 154. The secondary reaction chamber contains a colour-forming reagent which turns red in the presence of cyanogen chloride, the intensity of the colour increasing as the concentration of cyanogen chloride increases. Appropriate oxidising and colour-forming reagents are well-known and are commercially available.

The light receptor 152 is typically a transparent slug, such as a disc, having highly-polished end surfaces. It is mounted in the optic chamber 148 in such a way that its upstream end face is held in close optical contact with the ends of optic fibres forming a bundle 156. The latter is mounted in the end wall of the body 141 to extend through the chamber portion 147.

The two reagents are permanently held in their respective chambers 144, 154, by any suitable means, not shown. Preferably, these chambers contain microporous beads (not shown) of a suitable material chemically inert to their intended environment, so as to increase permeability and the surface area available for each reaction. The beads in the colour-change chamber 154, soaked in the indicator reagent which is changing colour on contact with the cyanogen compound, will themselves appear to change colour accordingly, thereby providing a large surface from which light, transmitted into the chamber 154 via optical fibres in the bundle 150, is reflected back to the appropriate fibres for receiving reflected light.

Where an arrangement such as that of FIG. 4 is used in the monitor shown in FIG. 2, the bundle 148 comprises the optical fibres 58 and 60, the colour-forming reagent being for example the indicator liquid mentioned earlier.

As will be clear from the description given above with reference to FIG. 1, the number of light sources, and therefore the number of colours used, is not restricted to two. There may for example be three colours, using three light sources, three data stores, and a sequence of dividing operations to produce divider output signals representing in turn the ratios A/B, B/C and A/C, wherein A,B and C are the output signals from the respective data stores. One example of a three-colour application lies in the field of photographic imaging, in which the apparatus is used to scan colour images to identify the pattern of absorption in the image of each primary colour. This pattern is converted, in the same way as has been described, into divider output signals which can then be used, employing known techniques, to produce a reconstituted image. In this case, the fibre optic bundles leading from the light sources may typically terminate in a mechanical scanner, the movement of which can be controlled from the timing means of the apparatus so that it commences a scan when the comparator output signal indicates that the selected light source has reached its steady, predetermined intensity level. The scanner may be arranged to be moved to another position when readings have been taken of all three colours, and so on through a large number of positions in intermittent motion until the scan is complete. At each position, the intensities of the reflected light in the three colours can be compared with each other, and (using for example circuitry of the same kind as that of FIG. 3 with a series of shift registers) compared also with those obtained at the last previous position. Alternatively the scanner may be arranged to carry out three complete scans, one for each colour, the reflected light intensity at each position being compared with the previous one. In this way a separate pattern can be built up for each colour.

Instead of the intermittent scanner movement implied above, the movement of the scanner may be continuous, at a constant known speed such that each cycle of operation of the electronic circuitry is related to a known area of the scanned image. In either case the scanner will preferably be controlled by the timing circuitry so that its movement is easily synchronised with the operation of the electronics.

The light sources may take any desired form according to the use for which the apparatus is designed. They may for instance comprise lamps giving a comparatively wide band of emission wavelengths, with narrow-band optical filters to transmit the chosen wavelength. For at least the application described in connection with the embodiment of FIGS. 2 to 4, however, LEDs are the preferred form of light source, as they have quite a narrow band of emission wavelength and exhibit an almost linear relationship between output light intensity and input current. The somewhat limited choice of available emission wavelengths using LEDs is no drawback for many applications, especially as LEDs are available for operation at wavelengths distributed quite widely over the visible spectrum. As an example, where the apparatus of FIG. 2 is used with a chemical sensor as described with reference to FIG. 4, the latter may be designed with a peak response in the range 545–560 nm, and with virtually no response above 620 nm. The LEDs in the clusters 54 and 52 can then typically be chosen with a wavelength of 555 (pure green) and 675 (red) respectively. LEDs are readily available at these wavelengths.

The apparatus is well adapted to ensure automatic rejection of spurious results. This is largely achieved in the apparatus of FIG. 2 by virtue of (a) the ADC enabling connection 106, which prevents the data registers 92 and 94 receiving reflected-light signals until the source intensities have been stablised, and (b) the fault monitoring unit 118 which disables the apparatus on a "fail safe" basis.

We claim:

1. Colour monitoring apparatus for monitoring a target, comprising:
    means for providing a plurality of light sources capable of intermittent operation, each light source having effectively a single emission wavelength different from that of another light source,
    timing means for causing each light source to operate in turn,
    a reflected light sensor, for receiving light transmitted by the sources and reflected from the target,
    a direct light sensor for providing an intensity output for light directly from each of said light sources,
    means for controlling intensity of each of said light sources and for stabilising the source intensity of the emission from each source at a predetermined level,
    a plurality of data stores, each arranged to receive from the reflected light sensor a signal representing the intensity of reflected light from a respective light source at a respective one of the emission wavelengths,
    divider means for receiving the information held in the data stores and for giving output signals each representing the ratio of two of said reflected light intensities, and
    signal processing means, said signal processing means including:
        means for receiving and storing a predetermined number of successive output signals from the divider means; and
        means for comparing said predetermined number of output signals to give an output signal representing one of a degree and rate of change in the ratios of the reflected light intensities, whereby a change in the ratios of the reflected light intensities corresponds to a change in the colour of the target such that the colour monitoring apparatus continuously monitors colour changes in the target.

2. Apparatus according to claim 1, further including enabling means, responsive to a signal from said means for controlling, for permitting a signal to be received from the reflected light sensor by a corresponding data store only when the source intensity of the corresponding light source has been stabilised.

3. Apparatus according to claim 1, wherein said timing means includes means for releasing the information held in each data store to the divider means at a predetermined time in each cycle of operation of the apparatus.

4. Apparatus according to claim 1 wherein said apparatus has two each of said light sources and data stores, with one source having a first emission wavelength wherein intensity of light at said first emission wavelength reflected by said target changes by an amount directly related to any change in color of said target and the other source having a second emission wavelength wherein intensity of light at said second emission wavelength reflected by said target is substantially unaffected by said change in color of said target, said divider including means for receiving information from both data stores at once and for performing a signal division calculation thereon in each cycle of operation.

5. Apparatus according to claim 1 wherein said light sources comprise clusters of light emitting diodes connected in parallel.

6. Apparatus according to claim 1, wherein said apparatus further includes said target and includes fibre optic connections that comprise a first connection, which is part of a closed energy loop, between the light sources and the direct light sensor, a second connection between the light sources and the target, and a third connection between the target and the reflected light sensor.

7. Apparatus according to claim 1 wherein said apparatus includes signal processing means for comparing two or more output signals, representing one of a degree and rate of change in the ratios of the reflected light intensities, with a predetermined reference value and for relaying said output signal only if two or more of said output signals are both or all above said reference value.

8. Apparatus according to claim 1, wherein said apparatus includes means, associated with each sensor, for monitoring temperature and for modifying the output signals from said each sensor to compensate for changes in temperature.

9. Apparatus according to claim 1 wherein the apparatus is for monitoring chemical changes and includes said target, the target being a chemical sensor including indicating means for changing colour in response to said chemical changes.

10. Apparatus according to claim 9, wherein said chemical sensor includes means for detecting a degree to which a specific gas is present.

11. Apparatus according to claim 2 wherein said means for controlling includes means for causing the source intensity of the light transmitted by each source to increase until it exactly equals the predetermined level and for preventing any further increase therein so as to stabilise the source intensity.

12. A method of continuously monitoring colour changes in a target, said method comprises the steps of:
(i) directing a first emission of light having a first emission wavelength from a first source towards the target and reflecting it from the target to a reflected light sensor so as to give first output signals responsive to the intensity of the reflected light and simultaneously directing the first emission to a direct light sensor to give second output signals responsive to the intensity of the emitted light;
(ii) comparing the second output signals with a known reference value, increasing the intensity of the light emitted from the first source, until it equals the reference value, and preventing any further increase therein so as to stabilise the first source intensity;
(iii) when the said first source intensity is stabilised, storing the first output signal then being given;
(iv) repeating steps (i) and (ii) but with a second emission of light from a second source having a second emission wavelength and a second source intensity, so that the reflected and direct light sensors give third and fourth output signals in place of the first and second output signals respectively;
(v) when the second source intensity is stabilised, storing the third output signal then being given;
(vi) dividing one of the stored first and third signals by the other to produce a fifth output signal representing the ratio of the intensities of reflected light derived form the first and second emissions;
(vii) timing the cycle comprising steps (i) to (vi) to take place over a predetermined period of time, and
(viii) repeating the cycle comprising steps (i) to (vi) at least once, receiving and storing the resulting succession of fifth output signals and comparing successive fifth output signals to give final output signals representing changes in the intensity of the light reflected from the target at at least one known wavelength,
the first and second emission wavelengths being chosen to be different from each other and each being effectively a signal wavelength.

* * * * *